United States Patent
Meyer

(10) Patent No.: US 9,915,716 B2
(45) Date of Patent: Mar. 13, 2018

(54) METHOD AND MAGNETIC RESONANCE APPARATUS FOR ESTABLISHING A MEASUREMENT PROTOCOL OF A MAGNETIC RESONANCE DATA ACQUISITION

(71) Applicant: Siemens Aktiengesellschaft, Munich (DE)

(72) Inventor: Heiko Meyer, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 377 days.

(21) Appl. No.: 14/688,281

(22) Filed: Apr. 16, 2015

(65) Prior Publication Data
US 2015/0369894 A1 Dec. 24, 2015

(30) Foreign Application Priority Data
Apr. 16, 2014 (DE) .................. 10 2014 207 308

(51) Int. Cl.
| | | |
|---|---|---|
| G05B 15/02 | (2006.01) | |
| G01R 33/54 | (2006.01) | |
| A61B 5/055 | (2006.01) | |
| A61B 5/00 | (2006.01) | |

(52) U.S. Cl.
CPC ............ *G01R 33/543* (2013.01); *A61B 5/055* (2013.01); *A61B 5/72* (2013.01); *G05B 15/02* (2013.01)

(58) Field of Classification Search
CPC .. G01R 33/543; G05B 15/02; G05B 19/0426; A61B 5/055

USPC ............................................ 700/90; 600/410
See application file for complete search history.

(56) References Cited

U.S. PATENT DOCUMENTS

| | | | | |
|---|---|---|---|---|
| 6,687,527 | B1 * | 2/2004 | Wu ...................... | G01R 33/546 324/318 |
| 6,762,605 | B2 | 7/2004 | Brinker et al. | |
| 6,912,415 | B2 * | 6/2005 | Kruger ................. | A61B 5/0555 600/407 |
| 7,145,338 | B2 * | 12/2006 | Campagna ............ | G01R 33/58 324/318 |
| 7,990,141 | B2 * | 8/2011 | Wohlfarth ............. | A61B 5/055 324/307 |
| 2003/0098687 | A1 * | 5/2003 | Arneth ................... | A61B 5/055 324/309 |
| 2003/0098688 | A1 * | 5/2003 | Brinker ................ | A61B 5/0555 324/309 |
| 2013/0023753 | A1 | 1/2013 | Kawamura et al. | |

* cited by examiner

*Primary Examiner* — Chun Cao
(74) *Attorney, Agent, or Firm* — Schiff Hardin LLP

(57) ABSTRACT

In a method and magnetic resonance apparatus for establishing at least one measurement protocol of a magnetic resonance measurement of an examination object, the measurement parameters necessary for the magnetic resonance measurement of the examination object are set, at least one absorption variable according to the measurement parameters set is established, and at least one measurement protocol is established that includes further measurement parameters according to the established at least one absorption variable. A characteristic variable can be established that indicates the ability to carry out the at least one measurement protocol according to the at least one established absorption variable.

7 Claims, 2 Drawing Sheets

METHOD AND MAGNETIC RESONANCE APPARATUS FOR ESTABLISHING A MEASUREMENT PROTOCOL OF A MAGNETIC RESONANCE DATA ACQUISITION

BACKGROUND OF THE INVENTION

Field of the Invention

The present invention concerns a method for establishing at least one measurement protocol for a magnetic resonance measurement of an examination object, as well as a computer non-transitory, computer-readable storage medium, as well as a correspondingly designed magnetic resonance apparatus.

Description of the Prior Art

Establishing a measurement protocol for a measurement with a magnetic resonance device is a widespread field of activity, especially in clinical practice.

In everyday clinical practice, explicitly establishing and setting necessary measurement variables, especially for efficient and targeted imaging, can be a complex problem.

SUMMARY OF THE INVENTION

An object of the invention is to provide an option with which it is possible to establish at least one measurement protocol while taking into consideration specific boundary conditions.

In accordance with the invention, a method for establishing at least one measurement protocol of a magnetic resonance measurement of an examination object includes the following steps:

a) setting the measurement parameters necessary for the magnetic resonance measurement of the examination object, b) establishing at least one absorption variable according to the measurement parameters set, and c) establishing at least one measurement protocol that includes further measurement parameters according to the at least one absorption variable established.

A "measurement protocol of a magnetic resonance measurement" as used herein means a set of parameters with which the magnetic resonance measurement is executed, such as, but not exclusively, geometrical parameters such as number of slices, slice thickness, number of segments or contrast parameters such as repetition time, echo time or flip angle.

An absorption variable is especially relevant as a measure for an absorption of electromagnetic fields in biological tissue, such as a specific absorption rate (SAR) for example. An absorption variable can also include a measure for an electrical power of components involved in the creation of electromagnetic fields.

The invention uses the establishment of at least one absorption variable according to previously set measurement parameters in order to establish at least one measurement protocol which includes further measurement parameters according to the at least one absorption variable established. Herein, "according to" is to be understood as distinguishing between cases which include different scenarios, depending on the established absorption variable. In this case "further measurement parameters of the established measurement protocol" are to be understood as those parameters which, when set at the magnetic resonance device provided for the magnetic resonance measurement, do not result in any significant change of the absorption variable previously established, but the opposite can also be the case. Measurement parameters can also be established which, when set at the magnetic resonance device provided for the magnetic resonance measurement, result in a maximum increase or reduction by a previously defined percentage of the absorption variable previously established.

This makes the effect of changing measurement parameters clearly visible to a user, especially the change of the absorption variable, which greatly enhances the user friendliness and also the security of the underlying measurement, as well as the safety of the examination object, as a rule a patient.

In a preferred embodiment, the method further includes establishing a duration of the time taken to carry out the at least one measurement protocol. This makes it evident how much time is required to carry out a set established measurement protocol. This saves time, increases efficiency in a clinical routine and also is more convenient for the user. In this case the duration of the at least one measurement protocol can also include pauses for example which are necessary to be able to carry out measurements.

In another embodiment, a characteristic variable is established, which indicates the ability to carry out the at least one measurement protocol according to the at least one established absorption variable. In this case a characteristic variable is to be understood for example as a yes/no and/or a green/red flag, that indicates for example which measurement protocol is able to be carried out, which measurement protocol is not able to be carried out or which measurement protocol can only be carried out in a specific mode of the magnetic resonance device or which measurement protocol can only be carried out after a specific waiting time or after a change of parameters of the measurement protocol. Such a characteristic variable enhances the safety of measurements with the magnetic resonance device and the operating convenience of users of the magnetic resonance device.

In a further embodiment the characteristic variable is a waiting time. In this case a waiting time is to be understood as that time for which it is necessary to wait before a specific measurement protocol is able to be carried out. This serves the safety of measurements with the magnetic resonance device, since it can be insured that a predetermined threshold value for the absorption variable is not exceeded. This likewise serves to optimize clinical workflow.

In another embodiment, the method includes a selection of the measurement protocol, wherein the further measurement parameters of the selected measurement protocol are set for the magnetic resonance measurement of the examination object. This enables a desired measurement protocol to be set at the magnetic resonance device in a simple, automated manner. This enhances user convenience and saves time.

In another embodiment, after the selection of the measurement protocol, the at least one absorption variable is re-established and the method begins again at method step b). Thus it is possible to establish at least one absorption variable again according to the previously set measurement parameters, since the absorption variable has changed under some circumstances through the newly set measurement parameters. This increases the safety of measurements with the magnetic resonance device and also allows, through the new start of the method, a renewed establishment of further measurement protocols according to the absorption variable last established.

In a further embodiment, the established absorption variable is displayed on a user device. In this case a user device is to be understood for example as a display and/or a monitor on which the absorption variable is presented graphically for example on a scale. This enhances an overview about the size of the absorption variable occurring, as well as the security of measurement with the magnetic resonance device. Likewise rapid acquisition of the absorption variable by clinical personnel or a user is possible.

In another preferred embodiment, the time for which the at least one measurement protocol is carried out is presented on a user device. This serves to provide an overview about the measurements with the magnetic resonance device and to optimize a clinical workflow. Likewise rapid acquisition of the absorption variable by clinical personnel or a user is possible.

The present invention also encompasses a magnetic resonance apparatus for establishing at least one measurement protocol of a magnetic resonance measurement of an examination object. The magnetic resonance apparatus is designed to implement the method described above.

The present invention also encompasses a non-transitory, computer-readable data storage medium that is able to be loaded into a memory of a programmable controller or a computer of a magnetic resonance apparatus. This storage medium is encoded with programming instructions (code) that cause the processor or computer to perform any or all of the previously described embodiments of the inventive method, when the code runs in the controller or computer of the magnetic resonance apparatus. The program code may possibly need program means, e.g. libraries and auxiliary functions, to realize the corresponding forms of embodiment of the method. The code can be source code, which still has to be compiled or interpreted, or can be executable software code that need only be loaded into the processor unit for execution.

The electronically-readable storage medium can be a DVD, a magnetic tape or a USB stick, on which electronically-readable control information, especially software, is stored.

The advantages of the inventive magnetic resonance apparatus and the inventive electronically-readable storage medium essentially correspond to the advantages of the inventive method that have been described above. The corresponding functional features of the method are embodied by corresponding physical modules, especially by hardware modules.

DESCRIPTION OF THE PREFERRED EMBODIMENTS

Figure 1:
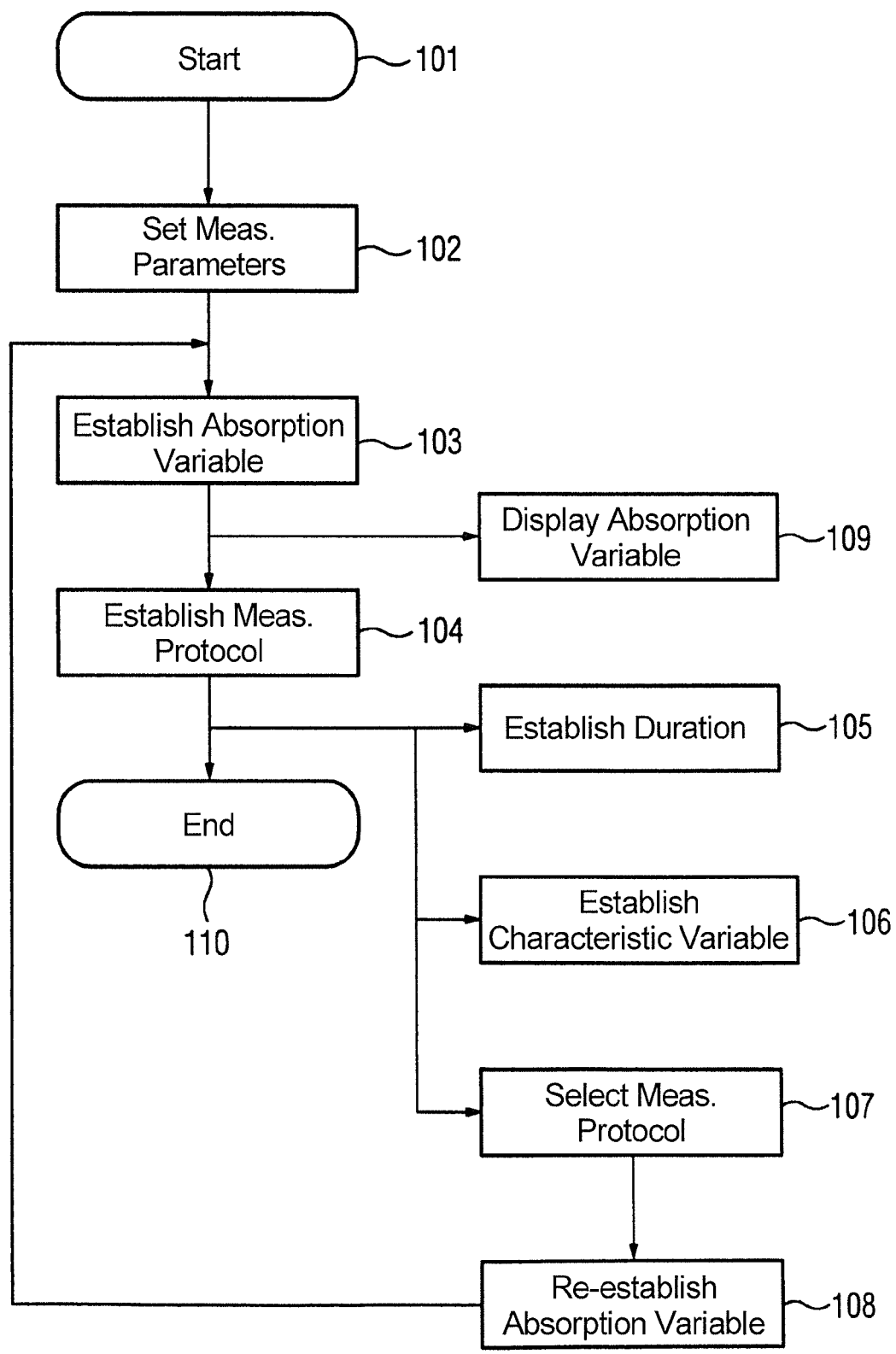
FIG. 1 is a flowchart of the inventive method.

FIG. 1 is a flowchart of the inventive method. The method comprises the method steps 101 to 110 wherein, in the description of the method steps 101 to 110, parts of the description are also used which include the corresponding reference characters introduced in conjunction with FIGS. 2 and 3.

The method steps 101 to 110 are executed here by a control computer 204 of a magnetic resonance apparatus 201.

A first method step 101 designates the start of establishing at least one measurement protocol of a magnetic resonance measurement of an examination object.

In method step 102 the measurement parameters necessary for the magnetic resonance measurement of the examination object, of a patient for example, are set.

Method step 103 designates the establishing of at least one absorption variable 301 according to the set measurement parameters.

Method step 109, an optional step after method step 103, designates a display of the established absorption variable 301 on a user device 202, 302. In this case a user device 202, 302 is to be understood for example as a display and/or a monitor on which the absorption variable is e.g. displayed graphically for an operator or for clinical personnel on a scale (see also FIG. 3).

In this case the time taken to perform the at least one measurement protocol can likewise be displayed on the user device 202, 302.

In method step 104 at least one measurement protocol is established which includes further measurement parameters according to the at least one established absorption variable 301. In this case further measurement parameters of the established measurement protocol are to be understood for example as those measurement parameters for which setting the parameters at the magnetic resonance device 201 provided for the magnetic resonance measurement does not result in any significant change in the previously established absorption variable, but the opposite can also be the case. Measurement parameters can also be established which, when set at the magnetic resonance device 201 provided for the magnetic resonance measurement, result in a maximum increase or reduction by a previously defined percentage or to a specific absorption value of the absorption variable previously established. This can be defined by an operator or also automatically by a programmable controller or a processing unit of a magnetic resonance device.

Method step 105, an optional step after method step 104, designates the establishment of a duration of the at least one measurement protocol. This means that the amount of time taken to execute a set established measurement protocol can be seen.

During a method step 106, which can likewise optionally be executed after method step 104, a characteristic variable is established which displays the ability to carry out the at least one measurement protocol according to the at least one established absorption variable 301. In this case a characteristic variable is to be understood for example as a yes/no and/or a green/red flag, which indicates for example which measurement protocol is able to be carried out, which measurement protocol is not able to be carried out or which measurement protocol is only able to be carried out in a specific mode of the magnetic resonance device 201 or which measurement protocol is only able to be carried out after a specific waiting time.

The characteristic variable can further comprise a waiting time. In this case a waiting time is to be understood as that time for which it is necessary to wait before a specific measurement protocol is able to be carried out.

Method step 107, likewise an optional step after method step 104, comprises selecting a measurement protocol, wherein the further measurement parameters of the selected measurement protocol are set for the magnetic resonance measurement of the examination object.

Thereafter, during a method step 108 after the selection of the measurement protocol, the at least one absorption variable 301 can be re-established, wherein the method then begins anew at method step 103. This makes it possible to again establish at least one absorption variable according to the previously set measurement parameters, since the absorption variable has been changed under some circumstances by the newly set measurement parameters.

A last method step 110 designates an end of establishing at least one measurement protocol of a magnetic resonance measurement of an examination object.

Figure 2:
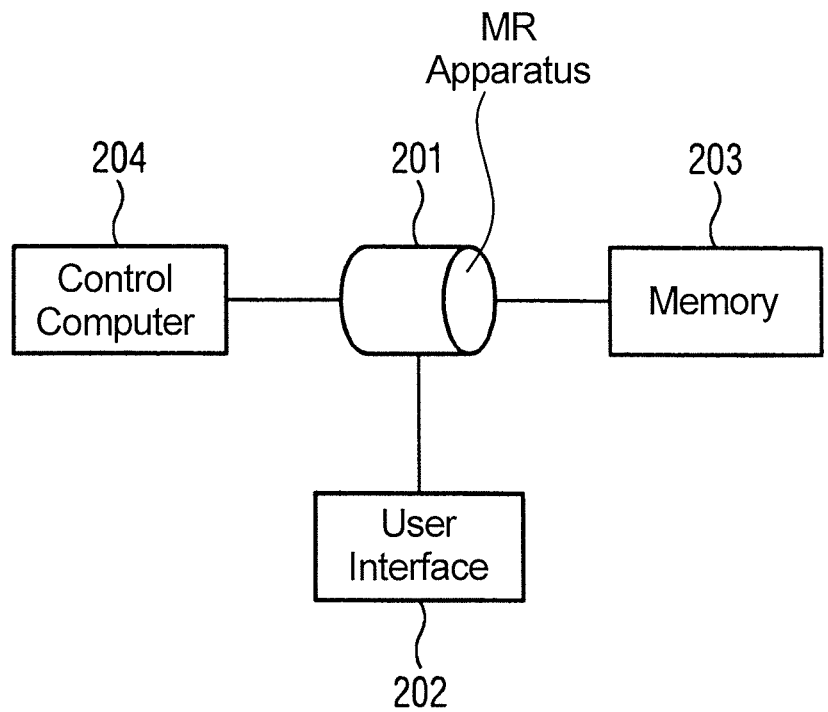
FIG. 2 schematically illustrates a magnetic resonance apparatus according to the invention.

FIG. 2 shows an inventive magnetic resonance apparatus 201. The magnetic resonance device 201 comprises a memory 203, a control computer 204 and a user device (interface) 202 and is designed for establishing at least one measurement protocol of a magnetic resonance measurement of an examination object.

The magnetic resonance apparatus 201 is embodied here as a pure magnetic resonance device. As an alternative the magnetic resonance device 201 can be a combined magnetic resonance-positron emission tomography apparatus or can include another device that is combined with a magnetic resonance apparatus, such as a linear accelerator, a radiation therapy device or an x-ray system.

Figure 3:
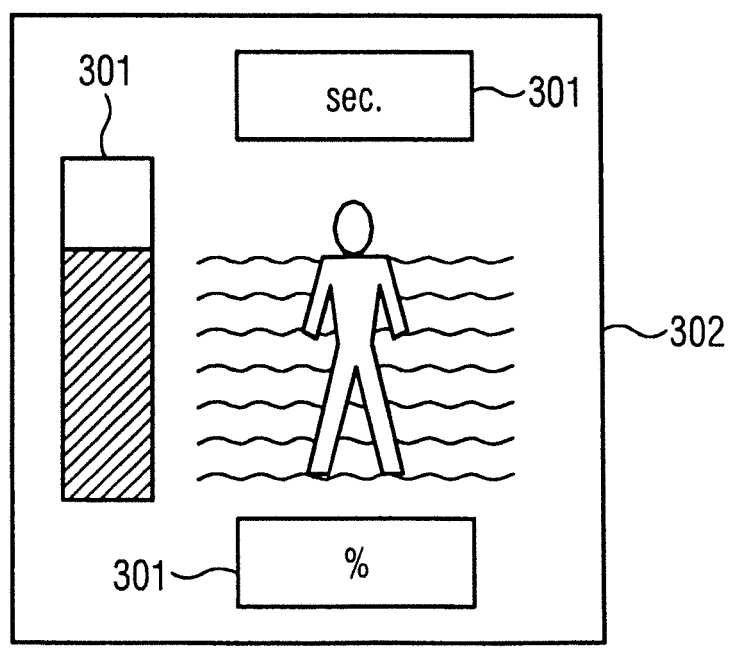
FIG. 3 shows an example of a display of an absorption variable on a user device in accordance with the invention.

FIG. 3 shows an example for displaying an absorption variable 301 on a user device 302.

In this case the absorption variable 301 comprises a specific absorption rate. The absorption variable 301 itself can be specified for example in the form of a ratio to the maximum load permitted by standards. In addition there can also be a display which is shown as a time interval in seconds. It then comprises the period of time in which a measurement can be made with the necessary measurement parameters set without exceeding the established absorption variable 301.

The absorption variable 301 can also be displayed as a percentage and then comprises the percentage of a remaining measurement time in relation to the overall measurement time in which a measurement with the necessary measurement parameters set can be made without exceeding the established absorption variable 301.

A further option for displaying the absorption variable 301 is to display it as a bar graphic. Thus the size of the bar represents a measurement time still remaining in which a measurement with the necessary measurement parameters set can be made without exceeding the established absorption variable 301.

Although the invention has been illustrated and described in greater detail by the preferred exemplary embodiments, the invention is not restricted by the disclosed examples and other variations can be derived therefrom by those skilled in the art, without departing from the scope of protection of the invention.

In summary the invention relates to a method for establishing at least one measurement protocol of a magnetic resonance measurement of an examination object, including the following steps:
 a) setting the measurement parameters necessary for the magnetic resonance measurement of the examination object,
 b) establishing at least one absorption variable according to the measurement parameters set,
 c) establishing at least one measurement protocol that includes further measurement parameters according to the at least one absorption variable established.

In an advantageous form of embodiment a characteristic variable is established which indicates the ability to carry out the at least one measurement protocol according to the at least one established absorption variable.

I claim as my invention:

1. A method for establishing at least one measurement protocol for executing a magnetic resonance (MR) data acquisition from an examination object, comprising:
 in a computer, setting measurement parameters for an MR data acquisition from an examination object to be executed by operating an MR scanner with said measurement parameters;
 entering a designation into said computer of a specific absorption rate (SAR) for said MR data acquisition;
 in said computer, generating at least one measurement protocol that includes further measurement parameters according to the designated SAR;
 from said computer, operating said MR scanner to execute said MR data acquisition using said measurement protocol that includes said further measurement parameters according to the designated SAR; and
 at a display in communication with said computer while MR data acquisition is being executed, displaying said designated SAR together with a remaining measurement time that can occur in said MR data acquisition without said designated SAR being exceeded.

2. A method as claimed in claim 1 comprising, in said computer, establishing a characteristic variable that indicates an ability of said MR scanner to execute said at least one measurement protocol according to said designated SAR.

3. A method as claimed in claim 2 wherein said characteristic variable includes a designation of a waiting time.

4. A method as claimed in claim 1 comprising establishing said at least one measurement protocol by selecting a measurement protocol that includes said further measurement parameters.

5. A method as claimed in claim 4 comprising after selecting said measurement protocol, establishing said SAR again, and repeating the step of establishing said at least one measurement protocol.

6. A magnetic resonance (MR) apparatus comprising:
 an MR scanner;
 a computer configured to set measurement parameters for an MR data acquisition from an examination object to be executed by operating said MR scanner with said measurement parameters;
 said computer being configured to receive a designation of a specific absorption rate (SAR) for said MR data acquisition;
 said computer being configured to generate at least one measurement protocol that includes further measurement parameters according to said designated SAR;
 said computer being configured to operate said MR scanner to execute said MR data acquisition using said measurement protocol that includes said further measurement parameters according to the designated SAR;
 a display in communication with said computer; and
 said computer being configured to display, while MR data acquisition is being executed, said designated SAR at said display together with a remaining measurement time that can occur in said MR data acquisition without said designated SAR being exceeded.

7. A non-transitory, computer-readable data storage medium encoded with programming instructions, said storage medium being loaded into a control computer of a magnetic resonance (MR) apparatus, and said programming instructions causing said control computer to:
 set measurement parameters for an MR data acquisition from an examination object to be executed by operating an MR scanner with said measurement parameters;

receive a designation of a specific absorption rate (SAR) for said MR data acquisition;

generate at least one measurement protocol that includes further measurement parameters according to said designated SAR;

operate said MR scanner to execute said MR data acquisition using said measurement protocol that includes said further measurement parameters according to the designated SAR; and display, at a display in communication with said control computer while MR data acquisition is being executed, said designated SAR together with a remaining measurement time that can occur in said MR data acquisition without said designated SAR being exceeded.

* * * * *